United States Patent [19]
Druais

[11] Patent Number: 5,755,725
[45] Date of Patent: May 26, 1998

[54] COMPUTER-ASSISTED MICROSURGERY METHODS AND EQUIPMENT

[75] Inventor: Herve Druais, Seyssinet, France

[73] Assignee: Deemed International, S.A., Gieres, France

[21] Appl. No.: 612,932
[22] PCT Filed: Sep. 6, 1994
[86] PCT No.: PCT/FR94/01050
  § 371 Date: Sep. 10, 1996
  § 102(e) Date: Sep. 10, 1996
[87] PCT Pub. No.: WO95/07055
  PCT Pub. Date: Mar. 16, 1995

[30] Foreign Application Priority Data

Sep. 7, 1993 [FR] France ............... 93 10624

[51] Int. Cl.$^6$ ............................................. A61B 19/00
[52] U.S. Cl. ............................................. 606/130
[58] Field of Search ............................................. 606/130

[56] References Cited

U.S. PATENT DOCUMENTS 5,251,127 10/1993 Raab ............... 606/130

FOREIGN PATENT DOCUMENTS

WO9104711 4/1991 WIPO.

*Primary Examiner*—Michael Buiz
*Assistant Examiner*—Julian W. Woo
*Attorney, Agent, or Firm*—Weiser and Associates P.C.

[57] ABSTRACT

Computer-assisted microsurgery equipment, of the type including an articulated tool support, with one of the ends being integral with a fixed reference system $R_c$. The system comprises cameras for determining the tool coordinates in said fixed reference system $R_c$, and an image data base wherein are recorded images from an imaging system in the image reference system $R_i$. The inventions characterized by having at least two sensors integral with the fixed reference system $R_c$ supplying an electrical signal depending on the patient reference position $R_p$ in the fixed reference system $R_c$, and a computer for matching the tool reference system $R_o$ with the patient reference system $R_p$ and the image reference system $R_i$ according to data from the bidimensional sensor, cameras for determining the coordinates of the tool in the fixed reference system $R_c$ and data from the image base. The computer supplies a signal for displaying the position of the tool in the image reference system $R_i$ on a monitor and for controlling the position and shifting of said tool as a function of the control signals from the control unit.

11 Claims, 1 Drawing Sheet

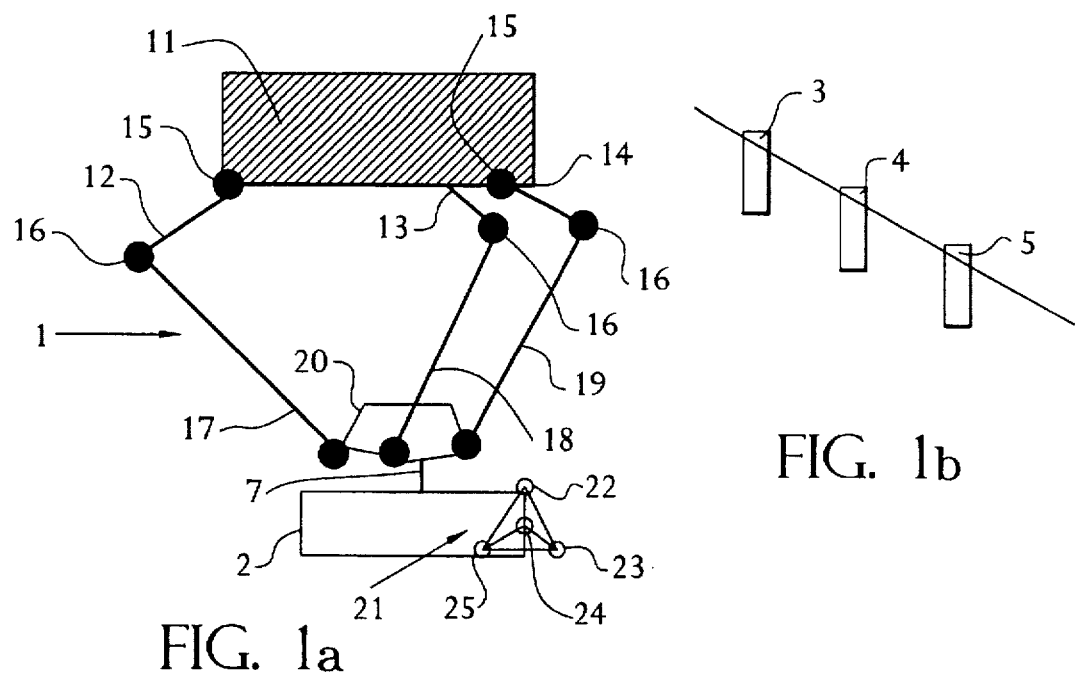
FIG. 1a
FIG. 1b
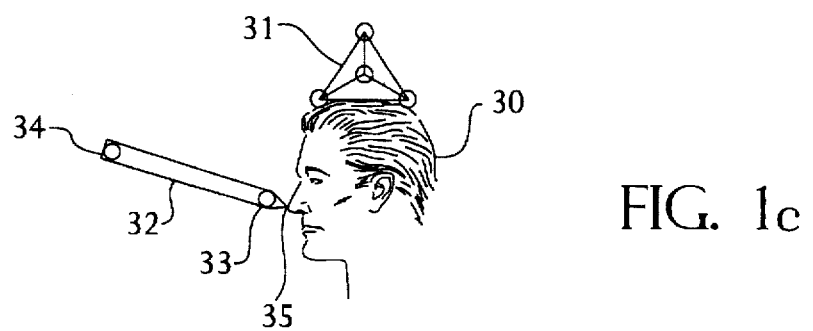
FIG. 1c
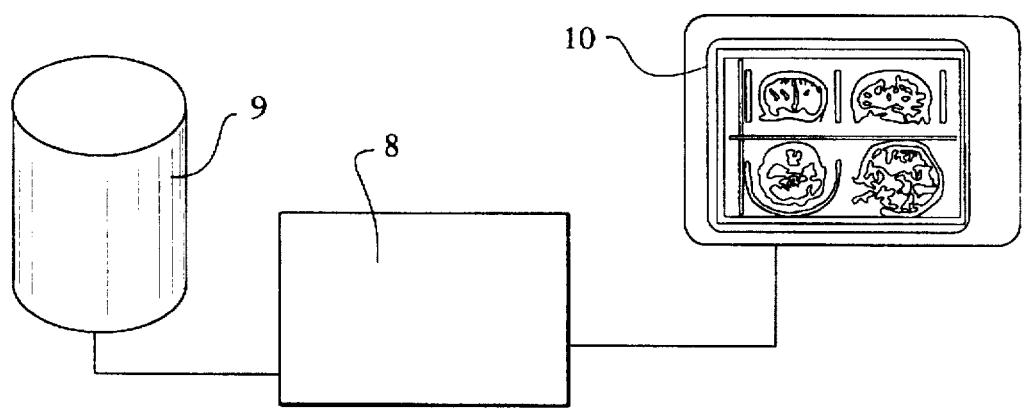
FIG. 1d

COMPUTER-ASSISTED MICROSURGERY METHODS AND EQUIPMENT

BACKGROUND OF THE INVENTION

1. Field of the Invention

The present invention relates to an installation for computer-assisted stereotactic microsurgery.

2. Description of the Related Art

Such installations are known in the state of the art. For example, French Patent FR 2651760 describes a method for the precise localization of a lesion and a device for the implementation of this method. The invention relates to a device and a method for the precise localization of a lesion. The method in accordance with the invention is characterized in that the organ to be examined is immobilized in the same position as that of the biopsy to be performed, tomodensitometric axial (XY) sections of the organ are performed through at least one transparent rectangle fitted with three nonsymmetrical concurrent opaque threads occupying determined positions in relation to the biopsy equipment, the lengths of the two segments (AB, AC) intercepted by said opaque threads for a selected lesion section are measured, at least one image is taken in the specimen removal position, the traces of the three opaque threads are reconstructed on said image and one transfers onto said image the lengths (AB, AC) of the measured segments in order to determine the lesional baseline corresponding to the selected lesional section.

Implementation of this method entails complete immobilization of the patient.

Another French patent published as number FR 2686499 describes a device for treating a target such as a lesion inside the body, using a marker element implanted in or near the target to direct the treatment of said target. This therapeutic device comprises:

means for treating the lesion, lesion localization means, with the localization means being linked, for example mechanically or electrically, to the therapeutic means, means for calculating the position of the lesion relative to the therapeutic means using the localization means, means for activating the therapeutic means.

The localization means identify the localization of at least one marker element implanted in the interior of the lesion. The calculation means calculate the position coordinates of the marker element (M0, M1, M2, M3) in relation to the therapeutic means which are used for the positioning of the mobile therapeutic means in the space of any position according to the X, Y, Z axes. This device enables precise treatment of the lesion.

Such a device requires intense presurgical preparation for its implementation.

French patent FR 2682778 describes a microscope for computer-assisted stereotactic microsurgery and a method for its operation. This microscope comprises detectors that detect optical data, a position identification system and a process control device that evaluates the signals from the said system. This system is an optics-based system integrated into the optical system of the microscope and it is provided with a device that converts the signals output by the device into a two-dimensional graphical representation.

Another patent of the prior art, patent PCT/FR090/00714, discloses an installation in which the principal reference system is linked to the patient's bed. The patient is immobilized in relation to the bed by a retention helmet or equivalent means. This document of the prior art discloses that the system has marked positioning means 2 linked in relation to the reference system R2 of the structures SNH and SR. For example, the head is fixed on the operating table.

This solution is not completely satisfactory because the retention means reduce the possible routes of access and impose constraints that are restrictive for the surgeon, who must assume that the position of the patient is fixed definitively as of the beginning of the intervention.

In addition, the operating table never exhibits absolute mechanical rigidity, and the correlation between the patient and the virtual images does not exhibit an adequate degree of precision for certain interventions.

Patent WO92/06644 describes a radiotherapy installation with means for attaining concordance between the radiation sources and previously obtained images. This document does not mention the use of a reference system corresponding to the fixed-reference system of the applicant's invention, which is additionally not necessary given the applications envisaged in this document of the prior art.

SUMMARY OF THE INVENTION

The object of the present invention is to resolve these drawbacks by proposing an installation of ergonomic use which makes it possible to separate the image-acquisition phase and the phase involving the exploitation of the images for surgical purposes.

In the state of the art, the image-acquisition systems for diagnostic purposes that do not require an intensive or traumatic intervention cannot be exploited for perioperative purposes. In fact, perioperative imaging requires the use of stereotactic techniques which are restrictive for the patient and for the operative personnel. These techniques notably involve a painful phase involving the implantation of a mechanical structure in the form of a frame which is indispensable for acquiring the images in relation to a known fixed reference system, to enable satisfactory calibration of the images, and to assure the immobilization of the patient's head, or more generally of the operative zone, in relation to a given reference system.

The goal of the invention is to assure a correlation between the digital images obtained by means of a medical imaging system with the patient so as to provide the surgeon with the data intended to guide his operative strategy in real time. Certain interventions require a precision of the correlation on the order of a millimeter or even less than a millimeter.

In order to attain this goal, the installation in accordance with the invention has an absolute reference system which is the fixed reference system Rr linked to a structure totally independent of the patient or of the imaging or visualization system.

Another goal of the invention is to enable surgeons to carry out image acquisition from a patient who is autonomous and not anesthetized, following a simplified procedure, at any time whatsoever of the hospitalization, or even in a different hospital facility, and possibly to use several complementary imaging techniques.

The invention relates more specifically to an installation of the type comprising an articulated tool-support, one end of which is integral with a fixed reference system $R_c$, with said system comprising means for determining the coordinates (position of a point and orientation of a direction vector) of the tool in said fixed reference system $R_c$, as well as an image data base in which are recorded the images originating from an imaging system in the image reference system $R_i$. The installation in accordance with the invention comprises at least two sensors integral with the fixed reference system $R_c$ outputting an electric signal that is a function of the position of the patient reference system $R_p$ in the fixed reference system $R_c$, and a computer for implementation of correspondence between the tool reference system Ro and the patient reference system $R_p$ and the image reference system $R_i$ as a function of the data stemming from said sensor, means for determining the coordinates of the tool in said fixed reference system $R_c$ and the data stemming from the image data base, said computer outputting a signal for the visualization of the position of the tool in the image reference system $R_i$, on a control screen, and for controlling the position and the displacements of the tool as a function of control signals output by a control unit.

This installation enables processing of one or more images acquired prior to the intervention, before the patient is transferred to the surgical unit, and the exploiting in real time of the images in relation to the progression of the surgical intervention.

The fixed reference system is a totally independent reference system and is decoupled from the patient reference system as well as the image reference system and the tool reference system. The fixed reference system is an absolute and permanent reference system. It is, for example, linked to a structural element of the surgical unit, for example the ceiling, the floor or a wall. This fixed reference system is selected in a manner so as to guarantee a permanent and stable reference system in which the various transformation matrices can be calculated in all situations, without limiting either the possible patient displacements or the possible tool displacements.

In accordance with a first variant, the sensors are constituted by at least two acquisition cameras integral with the fixed reference system $R_c$ and positioned such that their field of observation contains the surgical intervention zone.

Advantageously, the means for determining the coordinates of the tool in said fixed reference system $R_c$ are constituted by at least two acquisition cameras integral with the fixed reference system $R_c$ and positioned such that their field of observation contains the mobility space of the tool.

In accordance with a preferred mode of implementation, the installation comprises a geometrically defined trihedron, presenting at least four noncoplanar punctiform light sources integral with the tool carrier, with the mobility space of said trihedron being contained in the field of vision of the acquisition cameras.

Advantageously, the installation additionally comprises a geometrically defined trihedron, presenting at least four non-coplanar punctiform light sources integral with the patient, with the mobility space of said trihedron being contained in the field of vision of the acquisition cameras.

BRIEF DESCRIPTION OF THE DRAWINGS

Better comprehension of the invention will be gained from the description below which refers to the attached drawings in which:

FIGS. 1a–1d represent schematic views of the installation.

The installation in accordance with the invention comprises:
an articulated support (1);
a tool-carrier stage (2);
a set of three cameras (3, 4, 5);
reference trihedrons (21, 31);
a computer (8);
a device for storing digitized images (9);
a visualization screen (10).

The articulated support (1) comprises a base (11) integral with the fixed reference system $R_c$ which is, for example, the ceiling of the operating room.

The articulated support (1) is constituted in the described example by a system of the "three parallel delta axes" type. It comprises a first series of three arms (12, 13, 14) connected to the base (11) by independently controlled motors (15). The first series of three arms (12, 13, 14) is connected to a second series of arms (17, 18, 19) by ball-and-socket joints (16). The ends of the arms (17 to 19) are integral with a support (20) via rotational axes. The arms are spaced apart from each other by 120 degrees in a plane parallel to the base (11).

The end of the arms (17 to 19) is connected to a mechanism (20) comprising 3 rotational axes perpendicular in pairs, with the end of this latter rotational axis supporting a tool-carrier stage (2) comprising coupling means for a surgical instrument.

This support also comprises a trihedron (21) constituted by an assembly of four light points (22 to 25), for example, electroluminscent diodes, the geometric positioning of which is known precisely.

The displacement of this trihedron (21) is acquired by the set of cameras (3, 4, 5) which output an electric signal enabling the calculation at any moment of the position of the center of gravity of the trihedron (21) and its orientation, in the fixed reference system $R_c$, and thus to determine the passage matrix between the fixed reference system $R_c$ and the tool-carrier reference system $R_o$.

According to one mode of implementation, the electroluminscent diodes are powered sequentially, with detection being implemented in a synchronous manner.

The patient (30) also carries a trihedron (31) that allows the set of cameras (3, 4, 5) to output an electric signal enabling calculation at any moment of the position of the center of gravity of the trihedron (31) and its orientation, in the fixed reference system $R_c$, and thus to determine the passage matrix between the fixed reference system $Rk_c$ and the patient reference system $R_p$.

The geometrically defined trihedron can also be implemented in the form of implants installed on the patient before acquisition of the images, and located at four unaligned points. In this case, these implants are made of a material that allows detection by the imaging system(s) employed. The implants are, for example, made of titanium.

The method for using the installation for a surgical intervention is the following:

The patient, after preparation, enters into a first room in which image acquisition equipment is installed. In this room, one proceeds in a known manner to the instrumentation of the patient, the acquisition of the raw images and verification of the images obtained. The images are digitized and stored in an image data base. These images are then processed on a work station, in the absence of the patient, by calibration and segmentation of the images, indexing of the images and possible programming of the operative trajectories and strategies.

The patient is then transferred to the operating room.

In the operating room, one proceeds successively:
to the preparation of the patient;
to the instrumentation of the tool-carrier device;
to the installation of the patient, retaining the instrumentation installed in the image-acquisition phase;

to the complementary instrumentation of the patient;

to the implementation of correspondence among the various reference systems;

to the surgical intervention and the recording of the operative images.

Only the complementary instrumentation will be visible during the surgical intervention, with the initial instrumentation installed during the imaging phase being hidden under the sheets or the fields.

The patient is then transferred out of the operating room while the operative images are processed on a work station.

The image-acquisition procedure by the imaging system is more specifically comprised of:

shaving the patient if the intention is to instrument the head;

possibly anesthetize the patient before transforming him to the imaging room;

installing the trihedron (15) or the implants;

positioning the patient in the imaging system;

carrying out image acquisition;

verifying the images recorded in the image data base, notably with regard to the visibility of the reference frames on each of the images recorded, the definition and the data required for the subsequent surgical intervention;

removing the patient from the room.

The images are acquired by any known imaging means, for example, MRI, angiography, radiography, tomodensitometry, etc. The digitized images are stored in a data base which possibly can be accessed via a data network from a remote site.

The recorded images are then processed by proceeding to:

the calibration of the images according to the imaging specifications employed;

the segmentation of the images for 2D/3D or 3D exploitation;

the possible indexing of the reference frames for the implementation of correspondence;

the localization of the characteristic points of the images contained in the image data base, for exploitation during the operative phase, notably by the determination of the targets, possible routes of access and instrument trajectories, and possibly by the simulation of different strategies in 2D or 3D, and entry into the memory of the tested progression axes.

After this image processing step and the virtual exploitation of the image data base, the patient is transferred to the operating room.

In order for the surgeon to be able to exploit the previously acquired data, it is necessary to know the position and the relative orientation of the axis of the tool in relation to the images, in the intermediate reference frame corresponding to the intervention zone on the patient.

For this purpose, the invention enables the implementation of correspondence between the images acquired and linked to the patient, with the tool. The localization should be possible no matter the position of the tool and the patient.

The trihedron (21) that localizes the position of the tool is fixed in a removable or non-removable manner on the tool-carrier base. The attachment means should preferably not be articulated so as to guarantee permanence to the position of the trihedron (21) in relation to the tool support. Locking can be implemented with a clip connection.

Localization of the patient can be implemented in various manners: by installing a normalized rigid trihedron, or by installing unaligned implants, or by designating characteristics points of the surface of the patient, close to the operative zone, with a localization stylus.

This latter solution is comprised of employing a stylus-shaped pointer (32), carrying two reference points detectable by the camera system, and allowing designation, and thus input into the memory of the position of different characteristic points of the patient, of which it is possible to follow the displacements by shape recognition. The characteristic zones are, for example, the nose, the corners of the eyes or the chin.

Such a sensor (32) has a stylus shaped body terminated by a pointing zone (35) and comprising at least two light points (33, 34) enabling determination of the position and the orientation of the sensor (32) by analysis of the signals output by the cameras (3, 4, 5).

The implementation of concordance between the reference systems will be explained in greater detail below.

To facilitate comprehension, the following designations will be employed:

$^{a}P$ a defined point in the reference frame $R_a$;

$^{a}T_b$ the matrix of homogeneous transformation (4 lines, 4 columns) allowing expression in reference frame $R_a$ of the coordinates of a defined point in reference frame $R_b$, by the relation $^{a}P = {}^{a}T_b \, ^{b}P$.

In addition, the various reference frames cited are:

$R_o$ Reference frame of the tool;

$R_i$ Reference frame of the image;

$R_c$ Reference frame of the cameras;

$R_{pr}$ Reference frame of the sensor;

$R_{pg}$ Gross reference frame of the patient;

$R_{pc}$ Corrected reference frame of the patient;

$R_{mi}$ Geometric reference frame defined by at least 4 unaligned points (i variant of 1 to n);

$R_{m1}$ Geometric reference frame linked to the tool $R_{m2}$ Geometric reference frame linked to the patient.

In addition, $^{p_r}S$ will designate the surface defined by a set of points P, acquired in the sensor reference frame $R_{pr}$ and $^{i}S$ the surface defined by a set of points $P_j$ acquired in the image reference frame $R_i$.

Step 1: Implementation of concordance between the image reference frame and the patient reference frame The first step in the implementation of concordance between the reference systems consists of calculating the matrix $^{i}T_{p/pc}$ of passage between the image reference frame and the patient reference frame.

In accordance with one example of implementation of the installation, one uses a sensor (32) in order to mark known conspicuous points in the image reference frame $R_i$. The coordinates of the ends of the sensor (32) are known by construction, and by processing of the data output by the cameras (3, 4, 5) detecting the light points (33, 34) carried by the sensor.

It is thus possible to express the coordinates of the end (35) of the sensor (32) in the reference frame of the camera by the relation:

$$^{c}P_{sensor\ end} = {}^{c}T_{pr}\,^{pr}P_{sensor\ end}$$

and thus to calculate the matrix of passage between the camera reference system and the sensor reference system.

One uses, in addition, inserts or a trihedron (31) comprising in either case four unaligned points identifiable by the cameras (3 to 5) and defining the reference frame $R_{pc}$ of the patient.

These points $^{p}_j$ are known in the image reference frame $R_i$ and are measured with the sensor (32), in the sensor reference frame $R_{pr}$ in which their coordinates are $^{pr}P_j$. When the end of the sensor points on one of the points of the trihedron (31) or on one of the inserts, one has an identity relation between the two coordinates:

$$^{pr}_{\phantom{pr}j} = {}^{pr}R_{sensor\ end}$$

The transformation $^iT_{pr}$ is thus determined by a relation between the points $^iP_j$ from the image data base and the points $^{pr}P_j$ measured with the sensor. One uses the intermediate reference frame $kR_{m2}$ fixed by principle of use, in relation to the reference frame $R_{pc}$ and one determines the matrix of transformation $^iT_{m2}$. This matrix $^iT_{m2}$ is determined by a relation between the points $^iP_j$ of the image data base and the points $^{m2}P_j$ measured with the sensor.

In fact, when the end of the sensor (32) points on a point $P_j$, the following relation is verified:

$$^{m2}P_j = {}^{m2}T_c(t)^cT_{pr}(t)^{pr}P_{sensor\ end}$$

and one then determines $^iT_{m2}$ by the least squares method:

$$\text{Min} \sum_{j=1}^{n} \|({}^iP_j - {}^iT_{m2}{}^{m2}P_j)^2\|$$

According to an implementation variant, one avoids installation of a trihedron (31) or inserts, by using a surface correspondence method.

This requires two consecutive steps:

The first step consists of marking 4 conspicuous point on the patient (for example, the nose, the eyes, etc.). One is then in a situation similar to the preceding variant because one has available non-coplanar points $P_j$, the coordinates $^iP_j$ of which are known in the image reference frame $R_i$. The transformation $^iT_{pg}$ is determined by a relation between the points $^iP_j$ from the image data base and the points $^{pg}P_j$ measured with the sensor (32).

As above, one uses the intermediate reference frame $R_{m2}$ fixed in relation to the reference frames $RK_{pg}$ and $R_{pc}$.

One then obtains a "gross" transformation $({}^iT_{m2})_g$ which allows one to obtain a precision on the order of several millimeters which is insufficient for clinical use.

The second step consists of defining a corrected patient reference frame $R_{pc}$ by marking a multiplicity of conspicuous points in the vicinity of the intervention zone, using the sensor (32).

This operation makes it possible to bring into correspondence two surface.

- the real surface of the patient, defined by the acquisition made with the sensor $^{pr}S$ ($^{pr}P_j$) with $n \geq j \geq 4$, with the resolution improving as the magnitude of n increases;
- the surface $^iS$ linked to the image of the patient closest to the real surface defined in the image reference frame, and using the gross transformation $({}^iT_{m2})_g$ in selecting for this purpose only a part of the image data bank $^{pr}S\{^{pr}P_j\}$ with $n \geq j \geq 4$.

One then has the following relation:

$$^{m2}P_j = {}^{m2}T_c(t)^cT_{pr}(t)^{pr}P_{sensor\ end}$$

with $$^{pr}P_{sensor\ end} = {}^{pr}P_j$$

and one then determines $^iT_{m2}$ by the least squares method:

$$\text{Min}\Sigma\|(^iS\{P_j\} - {}^iT_{m2}{}^{m2}S\{^{m2}P_j\})^2\| \text{ with } n \geq j \geq 4$$

Step 2: Implementation of concordance between the tool reference frame and the fixed reference frame The following step of implementation of concordance between the reference systems consists of calculating the matrix $^cT_o$ of passage between the tool reference frame and the fixed reference frame.

The transformation $^{m2}T_o$ giving the relation between the tool reference frame $R_o$ and the fixed reference frame $R_{m1}$ is known by construction.

The coordinates of a point $^oP$ in the reference frame $R_o$ can be expressed in the reference frame $R_{m1}$ by the relation:

$$^{m1}P = {}^{m1}T_o{}^oP$$

The transformation $^cT_{m1}$ giving the relation between the fixed reference frame $R_{m1}$ and the reference frame $R_c$ is known in real time by infrared measurement. The coordinates of a point $^{m1}P$ in the reference frame $R_{m1}$ can be expressed in the reference frame $R_c$ by the relation:

$$^cP = {}^cT_{m1}(t)^{m1}P$$

The coordinates of a point $^oP$ linked to the tool can thus be expressed in real time in the fixed reference frame of measurement $R_c$ by the relation:

$$^cP = {}^cT_{m1}(t)^{m1}T_o{}^oP$$

Since the reference frame $R_o$ is defined by the trihedron (21), one thus obtains the relation in real time between the tool reference frame $R_o$ and the camera reference frame $R_c$.

Resolution of the equations enabling calculation of the transformation matrices

The fixed reference frame $R_{m1}$ is defined by at least 4 non-coplanar points $^{m1}P_1$ to $^{m1}P_4$.

The cameras (3 to 5) detect these four points in the camera reference system, in which their coordinates are $^cP_1$ to $^cP_4$.

One looks for the relation $^cT_{m1}$ such that:

$$^cP_j = {}^cT_{m1}{}^{m1}P_j$$

in which j=1 to 4

Theoretically, $$^cP_j - {}^cT_{m1}{}^{m1}P_j = 0$$

Thus, one looks for $^cT_{m1}$ that minimizes errors, from which:

$$\text{Minimum} \left( \sum_{j=1}^{4} \|(^cP_j - {}^cT_{m1}^{m1}P_j)^2\| \right)$$

The minimum is determined by derivation.

$^cT_{m1}$ is a homogeneous 4×4 matrix with 12 conspicuous elements $$^cT_{m1} = \begin{vmatrix} T_{11} & T_{12} & T_{13} & T_{14} \\ T_{11} & T_{22} & T_{23} & T_{24} \\ T_{31} & T_{32} & T_{33} & T_{34} \\ 0 & 0 & 0 & 1 \end{vmatrix}$$

One derives the relation $$S = \sum_{j=1}^{4} \|(^cP_j - {^cT_{m1}}{^{m1}P_j})\|^2$$

$$\frac{\delta s}{\delta T(k,l)} = 0$$

and one obtains a system of 3×4=12 equations with 12 unknowns for k=1 to 3: k being the line index
for l=1 to 4, l being the column index $$S = \sum_{j=1}^{4} \left[ \sum_{p=1}^{3} \left( {^cP_{j(p)}} - \sum_{q=1}^{4} {^cT_{m1(p,q)}}{^{m1}P_{j(q)}} \right)^2 \right]$$

Since $$\frac{\delta s}{\delta T(k,l)} = 0,$$

one can deduce the following relations:

$$\sum_{j=1}^{4} \left[ \sum_{p=1}^{3} \frac{\delta s}{\delta T(k,l)} \left[ {^cP_{j(p)}} - \sum_{q=1}^{4} {^cT_{m1(p,q)}}{^{m1}P_{j(q)}} \right]^2 \right] = 0$$

and $$\sum_{j=1}^{4} \left[ {^cT_{m1(k,l)}}{^{m1}P_{j(l)}} \left( {^cP_{j(k)}} - \sum_{q=1}^{4} {^cT_{m1(k,q)}}{^{m1}P_{j(q)}} \right) \right] = 0.$$

In this equation, one has:
$T_{k1}$
$T_{k1}$
$T_{k2}$
$T_{k3}$
$T_{k4}$
The equation system obtained by $$\frac{\delta s}{\delta T(k,l)} = 0$$

with k=1 to 3 and l=1 to 4 decomposes into 3 independent subsystems $$\frac{\delta s}{\delta T(1,l)} = 0$$

$$\frac{\delta s}{\delta T(2,l)} = 0$$

$$\frac{\delta s}{\delta T(3,l)} = 0$$

The resolution of this equation system is performed by an algorithm known by the computer of the installation in accordance with the invention, which will not be discussed in greater detail in the context of the present description, since the expert in the field is in a position to implement suitable data processing solutions.

Step 3: Implementation of concordance between the image reference frame and the camera reference frame The step following the implementation of concordance between the reference systems consists of calculating in real time the matrix ${^{m2}T_i(t)}$ of passage between the reference frame $R_{m2}$ linked to the patient with the image reference frame $R_1$.

The transformation ${^cT_{pr}}$ giving the relation between the reference frame $R_{pr}$ of the sensor (32) and the camera reference frame $R_c$ is known in real time by infrared measurement.

The coordinates of a point $^{pr}P$ in the reference frame $R_{pr}$ can be expressed in the reference frame $R_c$ by the relation:

$$^cP = {^cT_{pr(t)}}{^{pr}P}$$

The transformation ${^cT_{m2}}$ giving the relation between the fixed reference frame $R_{m2}$ and the reference frame $R_c$ is known in real time by infrared measurement. The coordinates of a point $^{m2}P$ in the reference frame $R_{m2}$ can be expressed in the reference frame $R_c$ by the relation:

$$^cP = {^cT_{m2}(t)}{^{m2}P}$$

in which $^{cpl}T_{m2}(t)$ is determined in a manner similar to $^cT_{m1}(t)$.

The coordinates of the end of the sensor (32) $^cP_{sensor\ end}$ are known in the reference frame $R_{pr}$ by construction.
They can be expressed by the reference:

$$^cP_{sensor\ end} = {^cT_{pr}(t)}{^{pr}P_{sensor\ end}}$$

Thus, they can be expressed in the reference frame $R_{m2}$ by the relation:

$$^{m2}P_{sensor\ end} = {^{m2}T_c}{^cT_{pr}(t)}{^{pr}P_{sensor\ end}}$$

Step 4: Implementation of concordance between the image reference frame and the tool reference frame The final step in the implementation of concordance consists of determining the relation between the reference frame $R_o$ image reference frame $R_1$.

For this, one knows:

Step 2: the position of the tool in the reference frame of the cameras by the transformation $^{m1}T_o$ (known by construction) and $^cT_{m1}(t)$ (determined in real time by infrared measurement);

Step 3: the correlation between the fixed reference frame $R_{m2}$ and the image reference frame $R_1$ by the transformation $^iT_{m2}$, determined during the implementation of correspondence.

The position of the reference frame $R_{m2}$ in relation to the fixed reference frame $R_c$ by the transformation $^{m2}T_{c(t)}$ which is the inverse of $^cT_{m2(t)}$, determined in real time by infrared measurement.

Thus, one obtains the transformation $$^iT_{o(t)} = {^iT_{m2}}{^{m2}T_{c(t)}}{^cT_{m1(t)}}{^{m1}T_o}$$

enabling the display in real time of the section corresponding to the point of interest.

One also obtains the transformation $^oT_{i(t)}$, inverse of $^iT_{o(t)}$, making it possible to automatically control the tool in real time in relation to a target defined in the image data base.

The invention is described above as a nonlimitative example. It is obvious that the Expert in the Field could propose diverse variants without going beyond the scope of the invention.

I claim:

1. A computer-assisted microsurgery installation, comprising:

(a) an articulated tool support, one end of which is integral with a fixed reference frame $R_c$;

(b) an image data base comprising images in an image reference frame $R_i$;

(c) at least two sensors, integral with the fixed reference frame $R_c$, supplying a signal that is a function of the position of a reference frame $R_p$ of a patient in the fixed reference frame $R_c$;

(d) a computer adapted to:
  (1) determine correspondence of a reference frame $R_o$ of the tool with the patient reference frame $R_p$ and the image reference frame $R_i$ as a function of the signal from the at least two sensors;
  (2) output a display signal for visualization of position of the tool in the image reference frame $R_i$ on a control screen; and
  (3) control position and displacements of the tool as a function of control signals originating from a control unit, wherein the fixed reference frame $R_c$ is independent of the patient reference frame $R_p$ and of the image reference frame $R_i$; and (e) means for determining coordinates of the tool in the fixed reference system $R_c$ based on data from the image data base.

2. The installation of claim 1, wherein the at least two sensors comprise at least two acquisition cameras integral with the fixed reference system $R_c$ and positioned such that their field of observation includes a surgical intervention zone.

3. The installation of claim 2, further comprising a first geometrically defined trihedron, presenting at least four non-coplanar punctiform light sources integral with the tool, with the mobility space of the first trihedron being contained in the fields of vision of the acquisition cameras.

4. The installation of claim 3, further comprising a second geometrically defined trihedron, presenting at least four non-coplanar punctiform light sources integral with the patient, with the mobility space of the second trihedron being contained in the fields of vision of the acquisition cameras during an entire operative phase.

5. The installation of claim 1, wherein the means for determining coordinates of the tool in the fixed reference system $R_c$ comprises at least two acquisition cameras integral with the fixed reference system $R_c$ and positioned such that their field of observation includes the mobility space of the tool.

6. The installation of claim 5, further comprising a first geometrically defined trihedron, presenting at least four non-coplanar punctiform light sources integral with the tool, with the mobility space of the first trihedron being contained in the fields of vision of the acquisition cameras.

7. The installation of claim 6, further comprising a second geometrically defined trihedron presenting at least four non-coplanar punctiform light sources integral with the patient, with the mobility space of the second trihedron being contained in the fields of vision of the acquisition cameras during an entire operative phase.

8. The installation of claim 1, further comprising an additional sensor comprising a pointing end and at least two light points, the positions of which in relation to the pointing end are determined geometrically by placing the additional sensor within the fields of vision of the at least two sensors.

9. The installation of claim 1, wherein:
  the at least two sensors comprise at least two acquisition cameras integral with the fixed reference system $R_c$ and positioned such that their field of observation includes a surgical intervention zone and the mobility space of the tool; and further comprising:
  a first geometrically defined trihedron, presenting at least four non-coplanar punctiform light sources integral with the tool, with the mobility space of the first trihedron being contained in the fields of vision of the acquisition cameras;
  a second geometrically defined trihedron, presenting at least four non-coplanar punctiform light sources integral with the patient, with the mobility space of the second trihedron being contained in the fields of vision of the acquisition cameras during an entire operative phase; and
  an additional sensor comprising a pointing end and at least two light points, the positions of which in relation to the pointing end are determined geometrically by placing the additional sensor within the fields of vision of the acquisition cameras.

10. A method for performing microsurgery using a microsurgery tool, comprising the steps of:
  (a) determining the position of the tool in a reference frame $R_c$ of a camera by a transformation $^{m1}T_c$, giving the relation between a reference frame $R_o$ of the tool and a fixed reference frame $R_{m1}$, and a transformation $^cT_{m1(t)}$, giving the relation between the camera reference frame $R_c$ and the fixed reference frame $R_{m1}$ determined in real time by optical measurement;
  (b) determining a transformation $^iT_{m2}$ giving the relation between an image reference frame $R_i$ and a fixed reference frame $R_{m2}$;
  (c) determining the position of the fixed reference frame $R_{m2}$ in relation to the camera reference frame $R_c$ by a transformation $^{m2}T_{c(t)}$ determined in real time by optical measurement;
  (d) calculating a transformation $^iT_{o(t)} = {^iT_{m2}}\,{^{m2}T_{c(t)}}\,{^cT_{m1(t)}}\,{^{m1}T_o}$, giving the relation between the image reference frame $R_i$ and the tool reference frame $R_o$, to display in real time a section corresponding to a point of interest indicating the position of the tool in relation to a prerecorded image; and
  (e) performing the microsurgery based on the real-time display of the section.

11. A method for controlling a microsurgery tool in relation to an image data base, comprising the steps of:
  (a) determining the position of the tool in a reference frame $R_c$ of a camera by a transformation $^{m1}T_o$, giving the relation between a reference frame $R_o$ of the tool and a fixed reference frame $R_{m1}$, and a transformation $^cT_{m1(t)}$, giving the relation between the reference flame $R_c$ and the fixed reference frame $R_{m1}$ determined in real time by optical measurement;
  (b) determining a transformation $^iT_{m2}$ giving the relation between an image reference frame $R_i$ and a fixed reference frame $R_{m2}$;
  (c) determining the position of the fixed reference frame $R_{m2}$ in relation to the reference frame $R_c$ by a transformation $^{m2}T_{c(t)}$ determined in real time by optical measurement;
  (d) calculating a transformation $^iT_{o(t)} = {^iT_{m2}}\,{^{m2}T_{c(t)}}\,{^cT_{m1(t)}}\,{^{m1}T_o}$, giving the relation between the image reference frame $R_i$ and the tool reference frame $R_o$;
  (e) calculating a transformation $^oT_{i(t)}$, which is an inverse of the transformation $^iT_{o(t)}$; and
  (f) automatically controlling the tool in real time in relation to a target defined in the image data base using the transformation $^oT_{i(t)}$.

* * * * *

Disclaimer

5,755,725 - Herve Druais, Seyssinet, France. COMPUTER-ASSISTED MICROSURGERY METHODS AND METHODS FOR USE WITH SAID EQUIPMENT. Patent dated May 26, 1998. Disclaimer filed November 12, 2014, by the assignee, SARIF BIOMEDICAL LLC.

I hereby disclaim the following complete Claims 10 and 11 of said patent.

*(Official Gazette, January 6, 2026)*

(12) INTER PARTES REVIEW CERTIFICATE (132nd)
United States Patent    (10) Number:    US 5,755,725 K1
Druais    (45) Certificate Issued:    May 13, 2016

(54) COMPUTER-ASSISTED MICROSURGERY EQUIPMENT AND METHODS AND METHODS FOR USE WITH SAID EQUIPMENT

(75) Inventor: Herve Druais

(73) Assignee: SARIF BIOMEDICAL LLC

Trial Number:

IPR2014-00753 filed May 14, 2014

Petitioners: Brainlab, AG; Varian Medical Systems, Inc.

Patent Owner: Sarif Biomedical LLC

Inter Partes Review Certificate for:

Patent No.: 5,755,725
Issued: May 26, 1998
Appl. No.: 08/612,932
Filed: Sep. 10, 1996

The results of IPR2014-00753 are reflected in this inter partes review certificate under 35 U.S.C. 318(b).

INTER PARTES REVIEW CERTIFICATE
U.S. Patent 5,755,725 K1
Trial No. IPR2014-00753
Certificate Issued May 13, 2016

AS A RESULT OF THE INTER PARTES REVIEW PROCEEDING, IT HAS BEEN DETERMINED THAT:

Claims 10 and 11 are disclaimed.

\* \* \* \* \*